(12) United States Patent
Jeong et al.

(10) Patent No.: US 9,702,949 B2
(45) Date of Patent: Jul. 11, 2017

(54) RF RECEIVING COIL AND MAGNETIC RESONANCE IMAGING APPARATUS INCLUDING THE SAME

(71) Applicant: Samsung Electronics Co., Ltd., Gyeonggi-do (KR)

(72) Inventors: Man Ho Jeong, Gyeonggi-do (KR); Kwang Hong Min, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 408 days.

(21) Appl. No.: 14/462,918

(22) Filed: Aug. 19, 2014

(65) Prior Publication Data

US 2015/0168511 A1  Jun. 18, 2015

(30) Foreign Application Priority Data

Dec. 12, 2013  (KR) .......................... 10-2013-0154504

(51) Int. Cl.
*G01R 33/34* (2006.01)
*A61B 5/055* (2006.01)
*G01R 33/3415* (2006.01)

(52) U.S. Cl.
CPC ........ *G01R 33/3415* (2013.01); *A61B 5/0555* (2013.01); *G01R 33/34007* (2013.01); *G01R 33/34084* (2013.01)

(58) Field of Classification Search
CPC .......... G01R 33/3415; G01R 33/34084; G01R 33/34007; A61B 5/0555
See application file for complete search history.

(56) References Cited

U.S. PATENT DOCUMENTS

| | | | |
|---|---|---|---|
| 2006/0255803 A1* | 11/2006 | Chu .................... | G01R 33/3415 324/318 |
| 2008/0129293 A1* | 6/2008 | Schnell ................ | A61B 5/0555 324/318 |
| 2009/0203990 A1* | 8/2009 | Noras ................. | G01R 33/3415 600/410 |
| 2013/0320981 A1* | 12/2013 | Bulumulla ........ | G01R 33/34084 324/318 |
| 2013/0320982 A1* | 12/2013 | Bulumulla ........ | G01R 33/34007 324/318 |

FOREIGN PATENT DOCUMENTS

| | | |
|---|---|---|
| JP | 2008-36400 A | 2/2008 |
| JP | 2008-178453 A | 8/2008 |
| JP | 2008-279233 A | 11/2008 |
| JP | 2011-185796 A | 9/2011 |

* cited by examiner

*Primary Examiner* — G. M. Hyder
(74) *Attorney, Agent, or Firm* — Cha & Reiter, LLC

(57) ABSTRACT

Disclosed are an RF receiving coil, which is retained in an interior receiving space of a patient table and is extractable from the patient table, and an MRI apparatus including the same. The MRI apparatus includes a patient table having an interior space, and at least one Radio Frequency (RF) receiving coil integrated with the patient table and retained in the space, the RF receiving coil being movable outward of the patient table.

15 Claims, 20 Drawing Sheets

RF RECEIVING COIL AND MAGNETIC RESONANCE IMAGING APPARATUS INCLUDING THE SAME

CLAIM OF PRIORITY

This application claims the benefit of Korean Patent Applications No. 10-2013-0154504, filed on Dec. 12, 2013 in the Korean Intellectual Property Office, the disclosure of which is expressly incorporated herein by reference.

BACKGROUND

1. Field

Embodiments of this disclosure relate to a Radio Frequency (RF) receiving coil to receive a magnetic resonance signal, and a magnetic resonance imaging (MRI) apparatus including the same.

2. Description of the Related Art

Generally, medical imaging apparatuses provide an image showing acquired patient information. Examples of medical imaging apparatuses include an X-ray apparatus, an ultrasonic diagnostic apparatus, a computed tomography apparatus, and an MRI apparatus.

Among the above enumerated apparatuses, the MRI apparatus takes an important position in the field of diagnosis using medical images because of its minimally restrictive imaging conditions and the excellent contrast provided with regard to soft tissues and various diagnostic information images.

Magnetic Resonance Imaging (MRI) is a technique of imaging physicochemical properties and density distribution of atomic nuclei by causing nuclear magnetic resonance in the nuclei of atoms, commonly hydrogen, in the human body or other object being imaged, using a magnetic field harmless to the human body and RF as non-ionizing radio waves.

Specifically, an MRI apparatus applies a constant frequency and energy to atomic nuclei in a state in which a constant magnetic field is created in a gantry, and converts energy emitted from the atomic nuclei into a signal to form an image showing the interior of an object.

In the MRI apparatus, an RF receiving coil is used to receive energy emitted from the atomic nuclei. The RF receiving coil is stored separately from a patient table and then connected to the patient table during magnetic resonance imaging.

SUMMARY

Disclosed is an RF receiving coil integrated with a patient table, and a magnetic resonance imaging apparatus including the same. The RF coil is movable outward of the patient table, e.g., via extraction of the RF coil from an interior space of the patient table.

In accordance with one aspect, an MRI apparatus includes a patient table having an interior space ("receiving space"), and at least one Radio Frequency (RF) receiving coil integrated with the patient table and retained in the space. The RF receiving coil is movable outward of the patient table.

In various embodiments:

The patient table may have at least one aperture formed in a face thereof, and one end of the RF receiving coil may be exposed through the opening.

The RF receiving coil may include a holder installed to the exposed end thereof to prevent the exposed end from being introduced into the receiving space through the aperture.

The RF receiving coil may be folded when retained in the receiving space.

The patient table may include a guide installed in the receiving space to guide movement of the RF receiving coil.

The RF receiving coil may include a fixing piece installed to one end thereof to fix the end to a surface of the patient table.

The patient table may include a first coupling piece provided at the surface thereof, the first coupling piece being coupled to the fixing piece to fix the RF receiving coil.

The magnetic resonance imaging apparatus may further include an auxiliary fixing member removable attached to the surface of the patient table to fix the RF receiving coil.

The auxiliary fixing member may include a second coupling piece coupled to the fixing piece to fix the RF receiving coil.

The magnetic resonance imaging apparatus may further include a cable provided in the patient table to transmit a magnetic resonance signal, received from an object by the RF receiving coil, to an image processor.

The RF receiving coil may include a peripheral vascular (PV) coil.

In accordance with another aspect, an RF receiving coil includes a plurality of coil panels including coils to receive magnetic resonance signals, and connectors to connect the coil panels to one another in a foldable manner, wherein the RF receiving coil is integrated with the patient table so as to be folded when retained in the patient table.

An example patient table for a magnetic resonance imaging apparatus includes a base portion and an upper face atop the base portion, where the upper face has at least one aperture. At least one RF receiving coil is integrated with the patient table and retained in a region of the base portion. The RF receiving coil is extractable and retractable through the at least one aperture.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Hereinafter, embodiments of the present invention will be described in detail with reference to the accompanying drawings.

Figure 1:
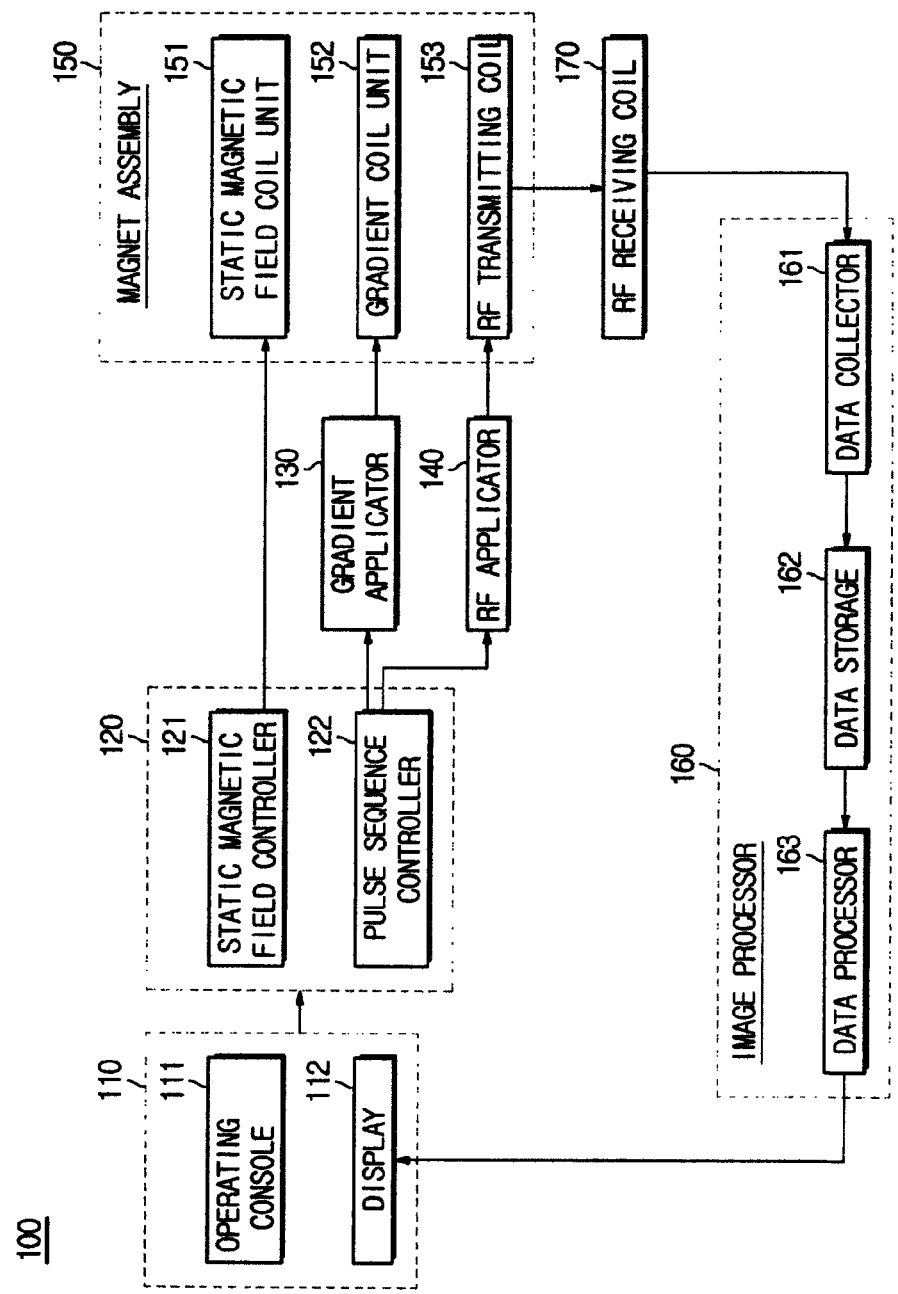
FIG. 1 is a functional block diagram of a magnetic resonance imaging apparatus in accordance with one embodiment.

FIG. 1 is a functional block diagram of an MRI apparatus in accordance with an embodiment. MRI apparatus 100 includes a magnet assembly 150 to create a magnetic field and cause resonance of atomic nuclei, a controller 120 to control operation of the magnet assembly 150, and an image processor 160 to produce a magnetic resonance image based on an echo signal generated from the atomic nuclei, i.e. a magnetic resonance signal. In addition, the MRI apparatus 100 includes an RF receiving coil 170 to receive a magnetic resonance signal from an object being imaged, induced by a magnetic field of the magnet assembly 150, and provides the same to the image processor 160.

The magnet assembly 150 includes a static magnetic field coil unit 151 to create a static magnetic field in an inner space of the magnet assembly 150, a gradient coil unit 152 to create a gradient magnetic field by providing the static magnetic field with a gradient, and an RF transmitting coil 153 to apply an RF pulse. When an object is located in the inner space of the magnet assembly 150, a static magnetic field, a gradient magnetic field, and an RF pulse may be applied to the object. Atomic nuclei of the object are excited by the applied RF pulse, and then return to ground state at varying rates, releasing energy that is used to generate an image.

The RF receiving coil 170 is separate from the magnet assembly 150 and receives electromagnetic waves emitted from the excited atomic nuclei, i.e. a magnetic resonance signal. In use, RF receiving coil 170 may be attached to the human body and thus is generally configured as a head coil, a neck coil, a waist coil, and the like to follow the contour of a human body region.

One example of the RF receiving coil 170 separable from the magnet assembly 150 is a surface coil to receive a magnetic resonance signal from an excited region of the object. The surface coil has a significantly high signal to noise ratio in a proximate region of the coil. The surface coil is smaller than a volume coil and takes the form of a 2-dimensional (2D) plane.

Another example of the RF receiving coil 170 is an array coil in which several surface coils are arranged in a 1D or 2D space to increase a receiving area. The array coil has a variable arrangement depending on an imaging region, and is classified into a head coil, a head and neck coil, a chest coil, a spine coil, an abdomen coil, a leg coil, and the like. The respective surface coils of the array coil have different relative positions, and thus each surface coil of the array receives a signal at a different phase. Accordingly, when reconstructing an image by synthesizing signals received by the respective surface coils, an image having a high signal to noise ratio may be acquired in consideration of the receiving phases of the surface coils.

The controller 120 includes a static magnetic field controller 121 to control the strength and direction of a static magnetic field created by the static magnetic field coil unit 151, and a pulse sequence controller 122 to control the gradient coil unit 152 and the RF transmitting coil 153 based on a pulse sequence.

The MRI apparatus 100 further includes a gradient applicator 130 to apply a gradient signal to the gradient coil unit 152, and an RF applicator 140 to apply an RF signal to the RF transmitting coil 153. The pulse sequence controller 122 may control the gradient applicator 130 and the RF applicator 140 to adjust an RF pulse to be applied to the atomic nuclei and a gradient magnetic field created in the inner space of the magnet assembly 150.

The RF receiving coil 170 is connected to the image processor 160, and the image processor 160 includes a data collector 161 to receive data related to a spin echo signal, i.e. a magnetic resonance signal generated from atomic nuclei for processing of the data and production of a magnetic resonance image. Image processor 160 further includes a data storage 162 to store the data received by the data collector 161, and a data processor 163 to produce a magnetic resonance image by processing the stored data.

The data collector 161 may include a preamplifier to amplify a magnetic resonance signal received by the RF receiving coil 170, a phase detector to detect a phase upon receiving the magnetic resonance signal from the preamplifier, and an A/D converter to convert an analog signal acquired via phase detection into a digital signal. The data collector 161 forwards the digital magnetic resonance signal to the data storage 162.

The data storage 162 has a data space for a 2D Fourier data. When all scanned data is completely stored, the data processor 163 implements 2D inverse Fourier transformation of data in the 2D Fourier space to reconstruct an image of an object 200. The reconstructed image may be displayed on a display 112.

In addition, the MRI apparatus 100 may include a user operating unit 110, which may receive a control instruction related to general operation of the MRI apparatus 100 from a user. In particular, the user operating unit 110 may produce a pulse sequence based on a received user instruction related to a scan sequence.

The user operating unit 110 may include an operating console 111 to allow the user to operate a system, and the display 112 to display a control state and an image produced by the image processor 160 to allow the user to diagnose a health state of the object 200.

Figure 2:
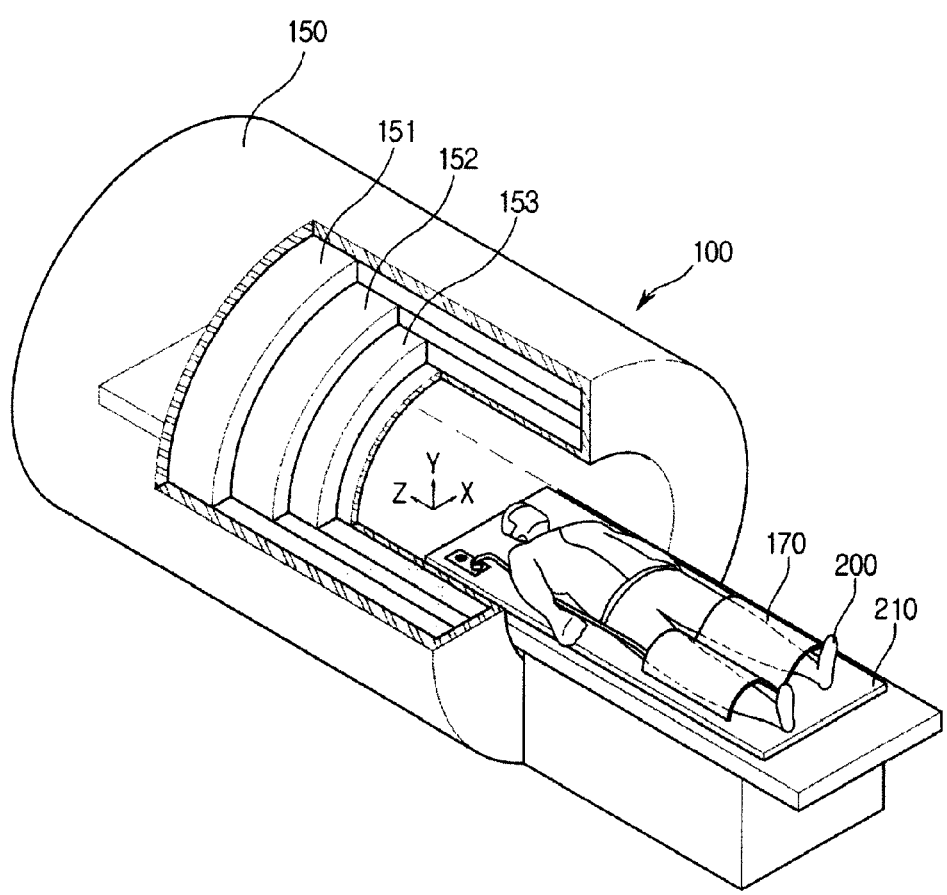
FIG. 2 is a partial cut-away view schematically showing an external appearance of the magnetic resonance imaging apparatus.
Figure 3:
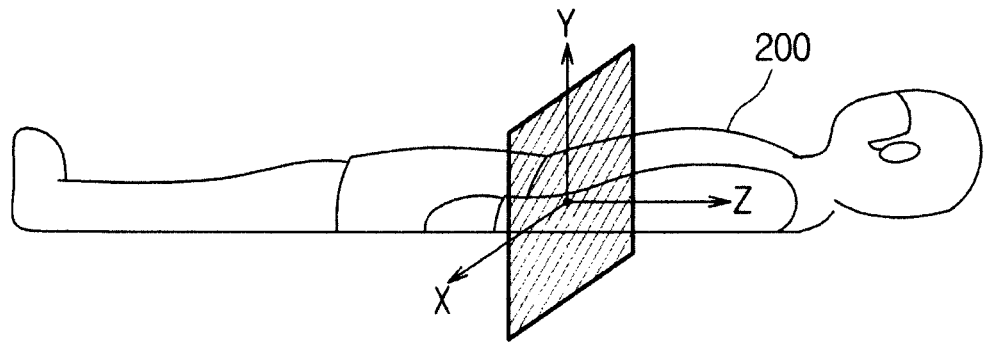
FIG. 3 is a view showing how an object to be imaged may be oriented within a cavity of the MRI apparatus with respect to an X-axis, Y-axis, and Z-axis.
Figure 4:
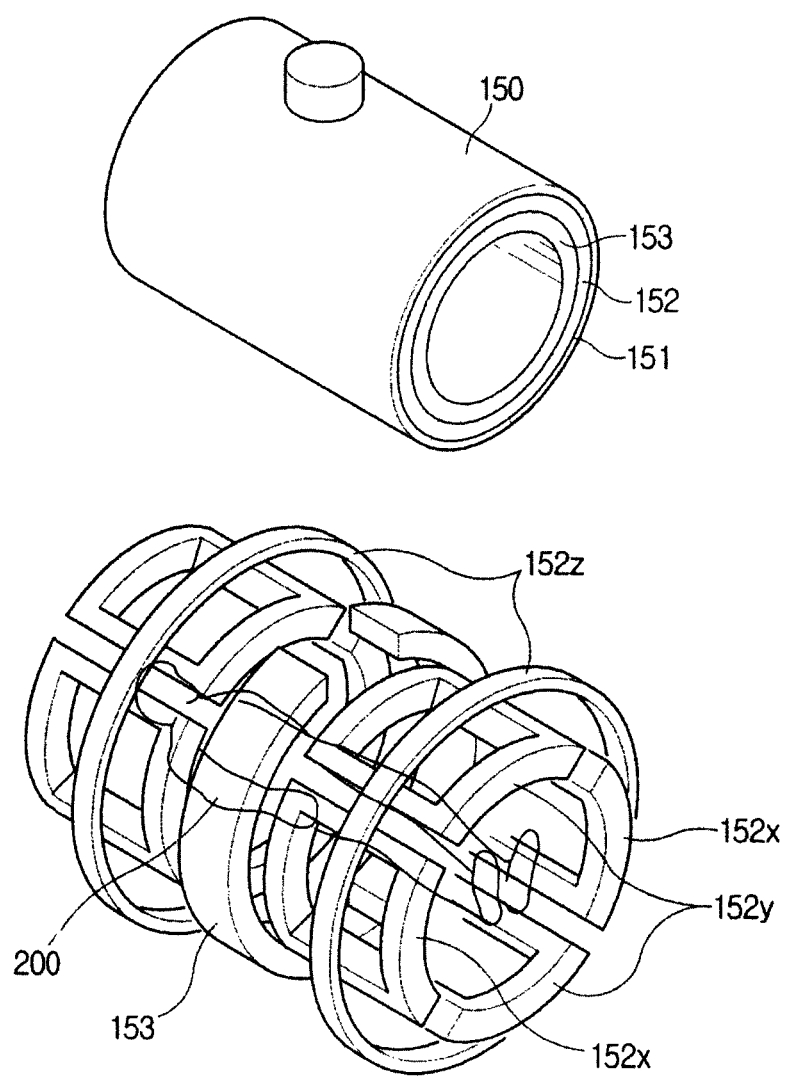
FIG. 4 is a view showing a configuration of a magnet assembly and a configuration of gradient coils.

FIG. 2 is a partial cut-away view schematically showing an external appearance of an example MRI apparatus 100. FIG. 3 is a view showing how an object to be imaged may be oriented within a cavity of the MRI apparatus with respect to an X-axis, Y-axis, and Z-axis. FIG. 4 is a view showing a configuration of the magnet assembly and a configuration of the gradient coil unit.

Referring collectively to FIGS. 1-4, the magnet assembly 150 takes the form of a hollow cylinder having an empty inner space. The magnet assembly 150 is referred to as a gantry, and the inner space is referred to as a cavity or bore.

A patient table 210 serves to transport the object 200 lying thereon into the cavity for acquisition of a magnetic resonance signal.

The magnet assembly 150 includes the static magnetic field coil unit 151, the gradient coil unit 152, and the RF transmitting coil 153. The static magnetic field coil unit 151 may be wound around the cavity. When current is applied to the static magnetic field coil unit 151, a static magnetic field is created in the inner space, i.e. in the cavity of the magnet assembly 150. The direction of the static magnetic field is generally parallel to a longitudinal axis of the magnet assembly 150.

When a static magnetic field is created in the cavity, atomic nuclei of atoms, more particularly hydrogen atoms of the object 200 are aligned in the direction of the static magnetic field, and precess about the direction of the static magnetic field. A precession speed of the atomic nuclei may be designated by a precession frequency, i.e. a Larmor frequency, which may be represented by the following Equation 1:

$$\omega = \gamma B_0 \quad \text{(eqn. (1))},$$

where, $\omega$ is a Larmor frequency, $\gamma$ is a proportional constant, and $B_0$ is the strength of an external magnetic field. The proportional constant is different per the kind of atomic nuclei, the unit of the strength of an external magnetic field is Tesla (T) or Gauss (G), and the unit of precession frequency is Hz.

For example, hydrogen has a precession frequency of 42.58 MHz within an external magnetic field of 1 T. Since hydrogen is the most abundant element in the human body, the MRI apparatus 100 attains a magnetic resonance signal using precession of hydrogen.

The gradient coil unit 152 provides the static magnetic field created in the cavity with a gradient, creating a gradient magnetic field.

As exemplarily shown in FIG. 3, an axis parallel to a vertical direction from the head to the feet of the object 200, i.e. an axis parallel to the direction of a static magnetic field may be referred to as the Z-axis, an axis parallel to a horizontal direction of the object 200 may be referred to as the X-axis, and an axis parallel to a vertical direction in the inner space may be referred to as the Y-axis.

Gradient magnetic fields in the X-axis, Y-axis, and Z-axis may generate 3D spatial information regarding a magnetic resonance signal. Thus, the gradient coil unit 152 includes three pairs of gradient coils.

As exemplarily shown in FIG. 4, generally, Z-axis gradient coils 152z are a pair of ring-shaped coils, and Y-axis gradient coils 152y are located above and below the object 200. X-axis gradient coils 152x are located at the left and right sides of the object 200.

Figure 5:
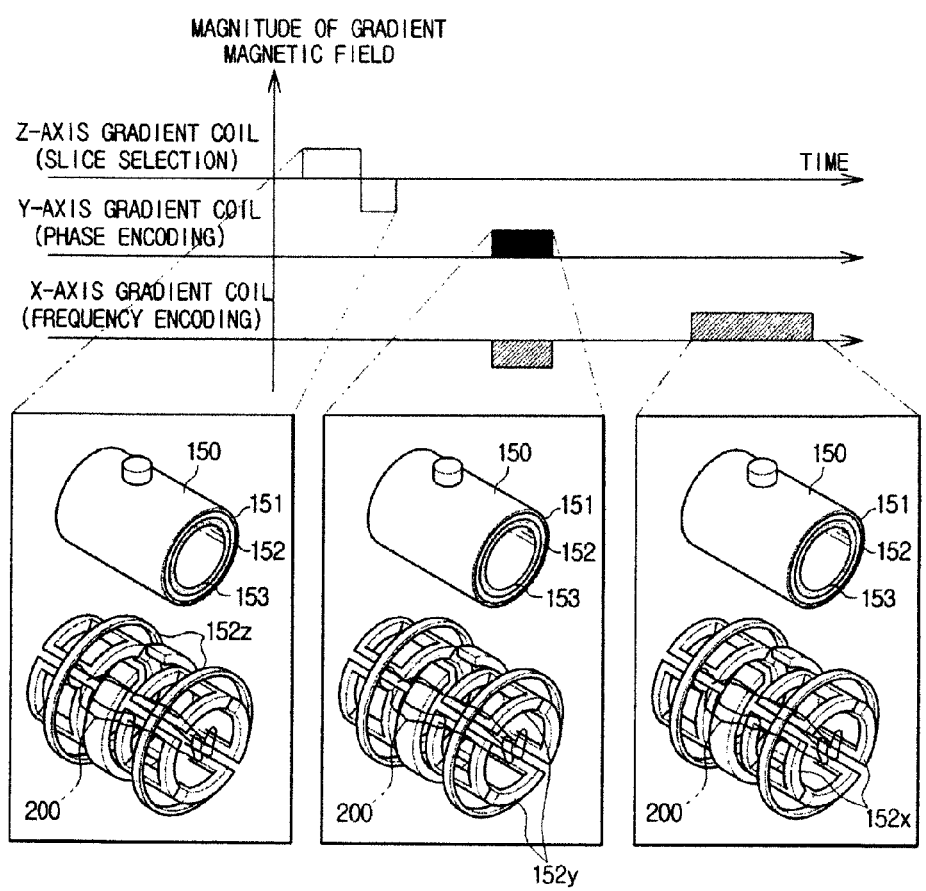
FIG. 5 is a view showing a pulse sequence related to operation of each gradient coil of a gradient coil unit.

FIG. 5 is a view showing a pulse sequence related to operation of each gradient coil of the gradient coil unit.

When direct current having opposite polarities is applied to the two Z-axis gradient coils 152z in opposite directions, a magnetic field in the Z-axis varies to create a gradient magnetic field.

As the gradient magnetic field is created by current applied to the Z-axis gradient coils 152z for a given time, a resonance frequency increases or decrease based on the magnitude of the gradient magnetic field. Then, when a high-frequency signal corresponding to a specific position is applied via the RF transmitting coil 153, only protons in a cross section corresponding to the specific position resonate. Thus, the Z-axis gradient coils 152z are used to select a slice.

As the gradient magnetic field created in the Z-axis increases, slice thickness decreases.

After the slice is selected by the gradient magnetic field created by the Z-axis gradient coils 152z, all spindles constituting the slice have the same frequency and the same phase, and thus are indistinguishable from one another. In this case, when a gradient magnetic field is created in the Y-axis by the Y-axis gradient coils 152y, the gradient magnetic field causes a phase shift such that rows of the slice have different phases.

More specifically, when the Y-axis gradient magnetic field is created, spindles of a row, affected by the great gradient magnetic field, undergo a phase shift to a high frequency, and spindles of a row, affected by the small gradient magnetic field, undergo a phase shift to a low frequency. When the Y-axis gradient magnetic field disappears, the respective rows of the selected slice attain different phases via a phase shift, and thus distinction of the rows may be possible. As such, the gradient magnetic field created by the Y-axis gradient coils 152y is used for phase encoding.

In brief, a slice is selected by a gradient magnetic field created by the Z-axis gradient coils 152z, and rows constituting the selected slice attain different phases and are distinguishable from one another by a gradient magnetic field created by the Y-axis gradient coils 152y. However, respective spindles of each row have the same frequency and the same phase, and thus are indistinguishable from one another. Further, when a gradient magnetic field in the x-axis is created by the X-axis gradient coils 152x, the X-axis gradient magnetic field provides the respective spindles of each row with different frequencies, enabling distinction of the respective spindles. The gradient magnetic field created by the X-axis gradient coils 152x is used for frequency encoding.

As described above, the gradient magnetic fields created by the X-axis, Y-axis, and Z-axis gradient coils are used respectively for slice selection, phase encoding, and frequency encoding, thereby achieving spatial encoding of spatial positions of the respective spindles.

The gradient coil unit 152 is connected to the gradient applicator 130. The gradient applicator 130 applies a current pulse to the gradient coil unit 152 in response to a control signal transmitted from the pulse sequence controller 122 to enable creation of the gradient magnetic fields. Accordingly, the gradient applicator 130 may be referred to as a gradient power source, and may have three drive circuits corresponding to the three pairs of gradient coils 152z, 152y, and 152x constituting the gradient coil unit 152.

When current is applied to the gradient coil unit 152 to generate the gradient magnetic fields, Lorenz force is generated, causing vibration of the coils. This vibration causes noise during magnetic resonance imaging. The degree of noise varies based on the shape and magnitude of a gradient magnetic field depending on imaging techniques, and is associated with characteristics of gradient magnetic coils.

As described above, atomic nuclei aligned by an external magnetic field may precess at a Larmor frequency, and the magnetization vector sum of the atomic nuclei may be represented by net magnetization M.

A Z-axis component of the net magnetization M is not measured, and only $M_{xy}$ may be detected. Thus, to acquire a magnetic resonance signal, it is desirable to excite atomic nuclei such that the net magnetization M is present in the XY plane. To excite atomic nuclei, an RF pulse, tuned to a Larmor frequency of the atomic nuclei, may be applied to a static magnetic field.

The RF transmitting coil 153 is connected to the RF applicator 140. The RF applicator 140 applies a high-frequency signal to the RF transmitting coil 153 in response to a control signal transmitted from the pulse sequence controller 122, causing the RF transmitting coil 153 to transmit an RF pulse to the interior of the magnet assembly 150.

The RF applicator 140 may include a modulation circuit to modulate a high-frequency signal into a pulse signal, and an RF power amplifier to amplify the pulse signal.

The RF receiving coil 170 may receive a magnetic resonance signal generated from atomic nuclei. As mentioned earlier, the RF receiving coil 170 provides a received magnetic resonance signal to the data collector 161 of the image processor 160 for processing of the signal and production of a magnetic resonance image. The data processor 163 produces a magnetic resonance image by processing data received by the data collector 161.

The data collector 161 may include an amplifier (or preamplifier) to amplify a magnetic resonance signal received by the RF receiving coil 170, a phase detector to detect a phase upon receiving the magnetic resonance signal from the amplifier, and an A/D converter to convert an analog signal acquired via phase detection into a digital signal. The data collector 161 provides the digital magnetic resonance signal to the data storage 162.

The data storage 162 has a data space for at least 2D Fourier data. When all scanned data is completely stored, the data processor 163 implements 2D inverse Fourier transformation of data in the 2D Fourier space to reconstruct an image of the object 200. The reconstructed image is displayed on the display 112.

A spin echo pulse sequence is mainly used to acquire a magnetic resonance signal from atomic nuclei. When a first RF pulse is applied to the RF transmitting coil 153, an RF pulse is transmitted once more at an appropriate time interval Δ t after application of the first RF pulse. Thereby, a magnetic resonance signal may be acquired as atomic nuclei exhibit strong transversal magnetization when the time Δ t has passed from application of the second RF pulse. This is referred to as a spin echo pulse sequence, and a time taken until the magnetic resonance signal is acquired after application of the first RF pulse is referred to as Time Echo (TE).

To what extent a proton has been flipped may be indicated by a movement angle from an axis at which the photon has been located prior to being flipped, and a 90° RF pulse or a 180° RF pulse appears based on a flip degree.

Meanwhile, the type of the RF receiving coil varies based on a region of an object (e.g., the human body) to be imaged. For example, types of RF receiving coils include a head coil, a spine coil, a shoulder coil, a breast coil, a torso coil, a knee coil, a peripheral vascular (PV) coil, a foot-ankle coil, or the like. Thus, there are various types of RF receiving coils and a desired one of the RF receiving coils is selected as needed.

Conventionally, various types of portable RF receiving coils are equipped nearby the MRI apparatus. However, a laborious task may be involved to move the RF receiving coil to the patient table to position it on the patient for use. Moreover, a cable connecting the patient table and the RF receiving coil to each other is exposed outward and may have a high risk of damage. In particular, in the case of a heavy PV coil, it may be very difficult to move the PV coil from the receiving space to the patient table.

To overcome these disadvantages, in accordance with the present embodiments, the RF receiving coil 170 may be integrated with the patient table 210. Thus, the integrated RF receiving coil 170 may be normally located within an interior of the patient table 210, and may be extracted from the patient table 210 as needed.

Figure 6A:
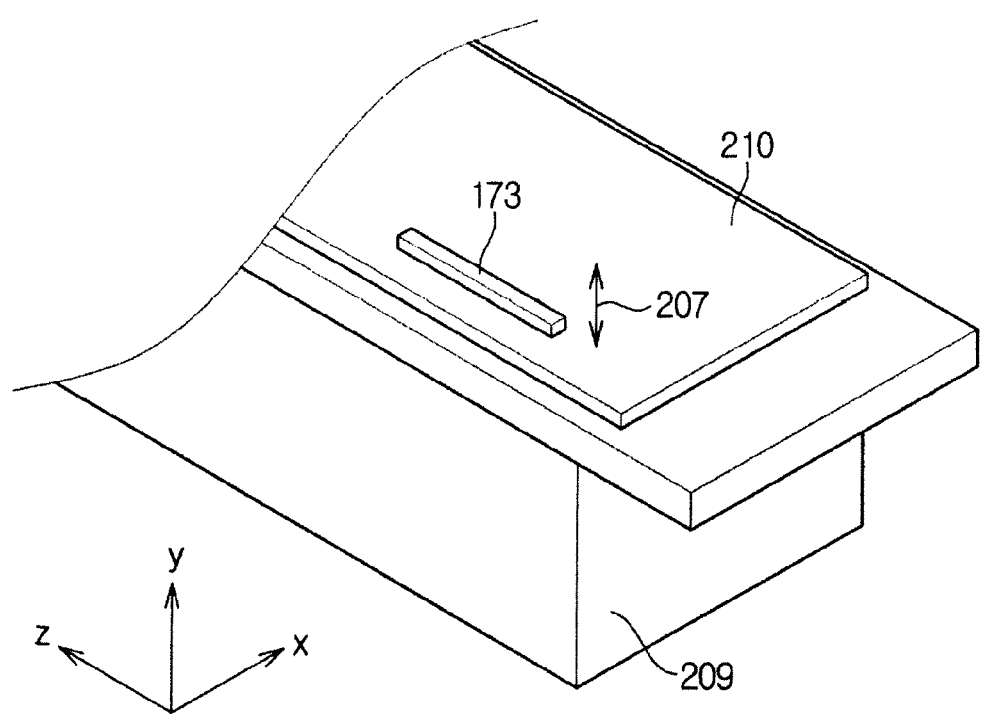
FIG. 6A and FIG. 6B are views illustrating an embodiment of an RF receiving coil integrated with a patient table of an MRI apparatus.
Figure 6B:
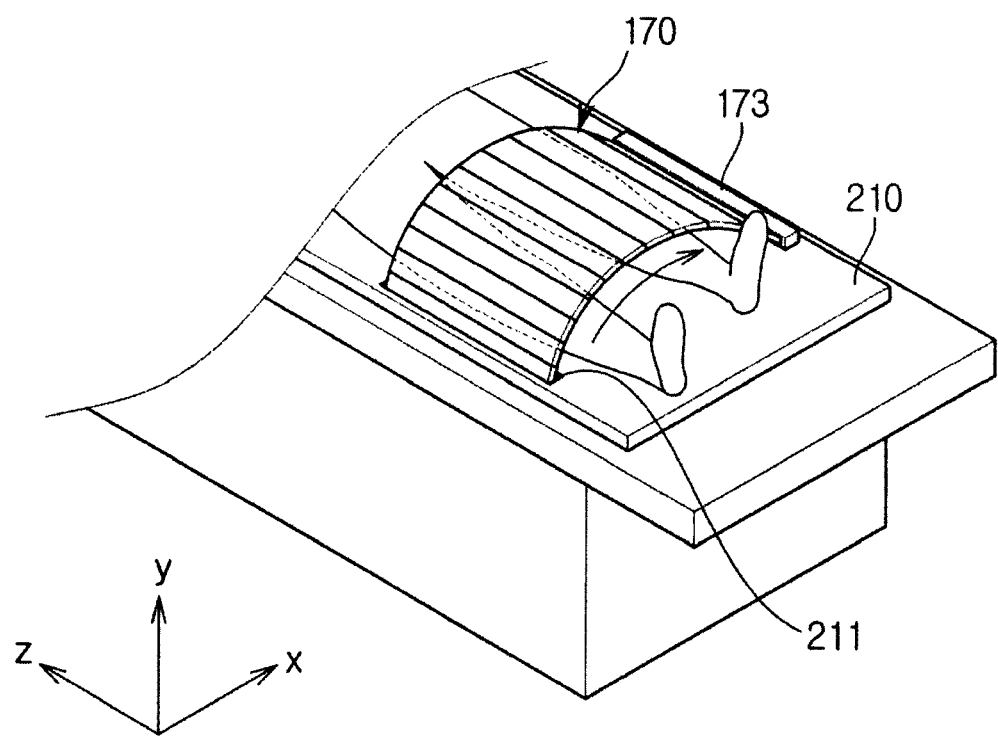

FIGS. 6A and 6B are views illustrating an embodiment of the RF receiving coil 170 integrated with the patient table 210. FIG. 6A illustrates the embodiment with the RF receiving coil in a retracted position while FIG. 6B illustrates the embodiment with the RF receiving coil in an extracted position during use with a patient.

In FIG. 6A, only a holding part, 173, of the RF receiving coil 170 is shown, as the remaining part of coil 170 is retained within a lower (base) portion 209 of the patient table 210. As shown in FIG. 6B, the coil 170 may be extracted through the upper face of the table 210 through pulling or other extraction means, so as to surround a desired portion of the patient to be imaged. In FIG. 6A, the RF receiving coil 170 may be extracted via initial movement in a direction designated by an arrow 207.

Figure 8A:
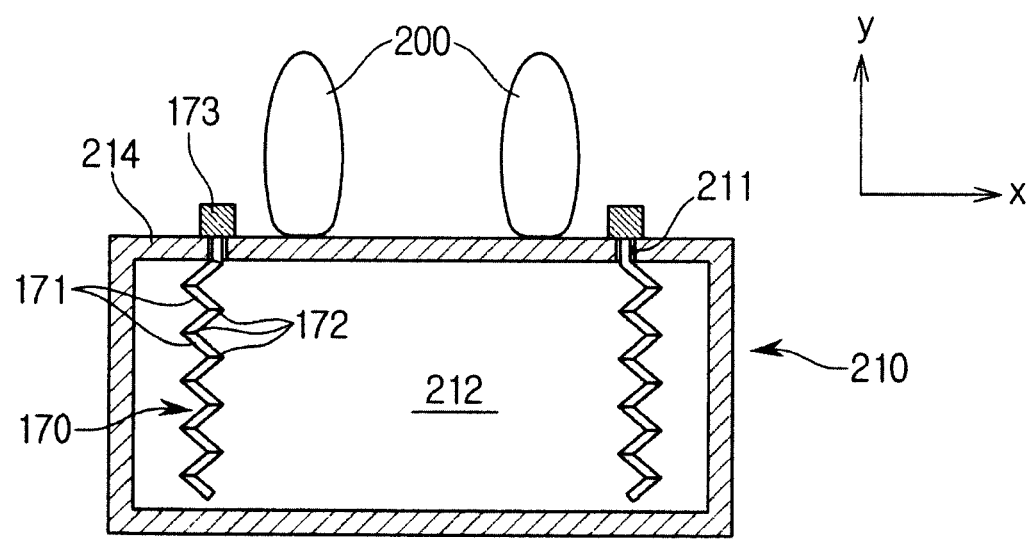
FIG. 8A and FIG. 8B are views illustrating one embodiment with regard to reception of the RF receiving coil, integrated with the patient table, in an interior receiving space of the patient table.

Referring momentarily to the cross-sectional or end view in FIG. 8A, a receiving space 212 may be defined in the patient table 210. The RF receiving coil 170 may be located and retained/stored in the receiving space 212 so as to be integrated with the patient table 210. As exemplarily shown in FIG. 6A, one end of the RF receiving coil 170 may be exposed from one face of the patient table 210, and a hidden portion of the RF receiving coil 170 may be received in the interior receiving space 212 of the patient table 210.

As seen in FIG. 6B, patient table 210 may have an opening (aperture) 211 in one face thereof (exemplified as the upper face 214 in the various figures herein). One end of the RF receiving coil 170 (e.g., the holder 173) may be exposed through the opening 211. In addition, the RF receiving coil 170, received in the interior receiving space 212 of the patient table 210, may be extracted from of the patient table 210 through the opening 211 during use in the MRI procedure, and retracted back within the table 210 during non-use. The holder 173 may prevent the outwardly exposed end of the RF receiving coil 170 from retracting back into the interior receiving space 212 of the patient table 210. To this end, the holder 173 may have a different shape than the opening 211.

In addition, when the user attempts to extract the RF receiving coil 170 from patient table 210, the holder 173 may serve as a grip that the user hand grips. To ensure an easy user grip, the holder 173 may include a grip recess or a handle.

In the embodiment of FIGS. 6A and 6B, a single RF receiving coil 170 is integrated with the patient table 210. FIG. 6B illustrates a state in which the single RF receiving coil 170, received in the receiving space 212 of the patient table 210, is extracted from the patient table 210. When the handle 173 is pulled, or force is otherwise applied to the end of the RF receiving coil 170 exposed outward of the patient table 210 to push the RF receiving coil 170 away from the patient table 210, the RF receiving coil 170 received in the interior receiving space 212 of the patient table 210 may be moved outward of the patient table 210.

During MRI imaging, RF receiving coil 170 may receive a magnetic resonance (MR) signal generated from the object 200. The quality of the received MR signal may be higher as the RF receiving coil 170 comes into closer contact with the object 200. Thus, the RF receiving coil 170, extracted from the patient table 210, comes into close contact with the object 200 lying on the patient table 210, thereby receiving an MR signal from a closely contacted region of the object 200. As illustrated in FIG. 6B, when the RF coil 170 is extracted and surrounds a portion of the object 200, it may be suitable fastened to a point on the opposing side of the patient table 200 (the right side opposite the left side with aperture 211 in the example).

As noted earlier, in conventional MRI apparatuses, the RF receiving coil is separate from the patient table, and if heavy, such as a PV coil, it may be difficult to move. By contrast, the RF receiving coil 170 integrated with the patient table 210 is normally present in the interior receiving space 212 of the patient table 210, and may be extracted from patient table 210 during the MRI process to closely contact a desired region of the object so as to receive an MR signal from the corresponding region. This may eliminate a laborious task to move the RF receiving coil from the external receiving space to the patient table.

Figure 7A:
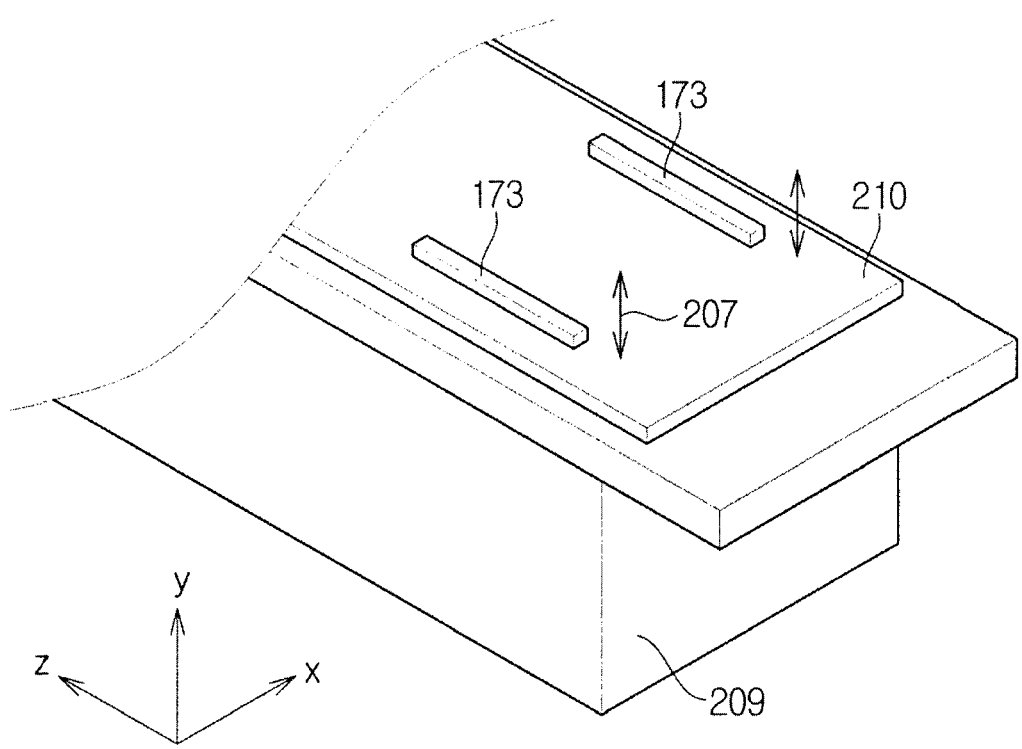
FIG. 7A and FIG. 7B are views illustrating another embodiment of a patient table of an MRI apparatus, in which plural RF receiving coils are integrated with the patient table.
Figure 7B:
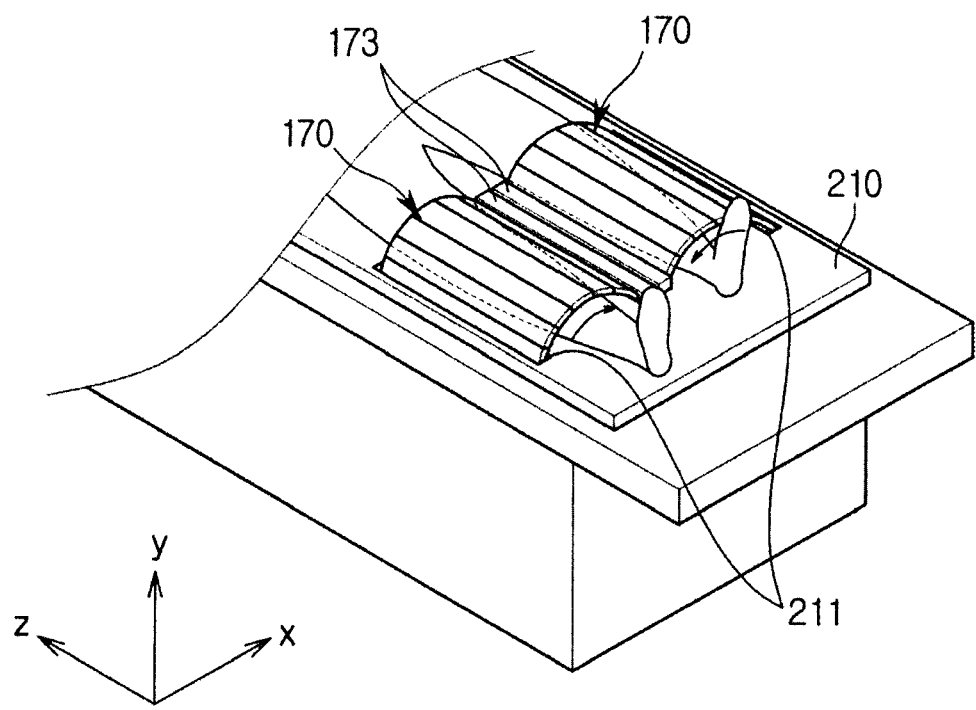

FIGS. 7A and 7B illustrate another embodiment of a patient table of an MRI apparatus, in which plural RF receiving coils are integrated with the table. In this embodiment, two RF receiving coils 170 are employed. FIG. 7A shows a retracted state of the RF receiving coils, while FIG. 7B shows extracted states of the coils surrounding a portion of an object 200 undergoing MRI imaging.

As exemplarily shown in FIG. 7A, two RF receiving coils 170 may be moved in a direction designated by the arrows 207 so as to be extracted from/retracted into the patient table 210. Similar to the embodiment of FIGS. 6A, 6B, each of the two RF receiving coils 170 of FIGS. 7A, 7B may be housed in the interior receiving space 212 of the patient table 210 except for an outwardly exposed end thereof (e.g., handles 173).

When a plurality of RF receiving coils 170 are housed in the receiving space 212, plural openings 211 for the respective RF receiving coils 170 may be provided. FIG. 7B illustrates the case in which two openings 211 are formed in one surface of the patient table 210 to allow the two RF receiving coils 170 to be extracted from or otherwise moved outward of the patient table 210. As illustrated, when each RF coil 170 is extracted sufficiently to surround a desired portion of the object 200, it may be fixed at a central region of the table 200 in the width direction.

As mentioned above, the patient table 210 may have the openings 211 for movement of the respective RF receiving coils 170, and the RF receiving coils 170 may be moved outward of the patient table 210 through the openings 211. Thus, since the respective RF receiving coils 170 are movable to different positions at the outside of the patient table 210, it may be possible to use just one of the RF receiving coils 170 corresponding to a desired region of the object 200 to be imaged.

The respective RF receiving coils 170 of FIG. 7B are movable to surround both legs of the object 200 lying on the patient table 210. That is, the two RF receiving coils 170 received in the interior receiving space of the patient table 210 are moved outward of the patient table 210 to tightly surround the respective legs close thereto. Thereby, magnetic resonance signals from the legs may be acquired, and a magnetic resonance image may be produced based on the acquired magnetic resonance signals.

In the description above, the embodiments of the RF receiving coil 170 integrated with the patient table 210 viewed from the outside of the patient table 210 have been described with reference to FIGS. 6A and 6B and FIGS. 7A and 7B. Hereinafter, various embodiments with regard to reception of the RF receiving coil 170 in the interior receiving space 212 of the patient table 210 will be described with reference to FIGS. 8A and 8B, FIGS. 9A and 9B, and FIGS. 10A and 10B. For convenience of description, the following description assumes that two RF receiving coils 170, such as those in FIGS. 7A, 7B are disposed in the interior receiving space 212 of the patient table 210.

Figure 8B:
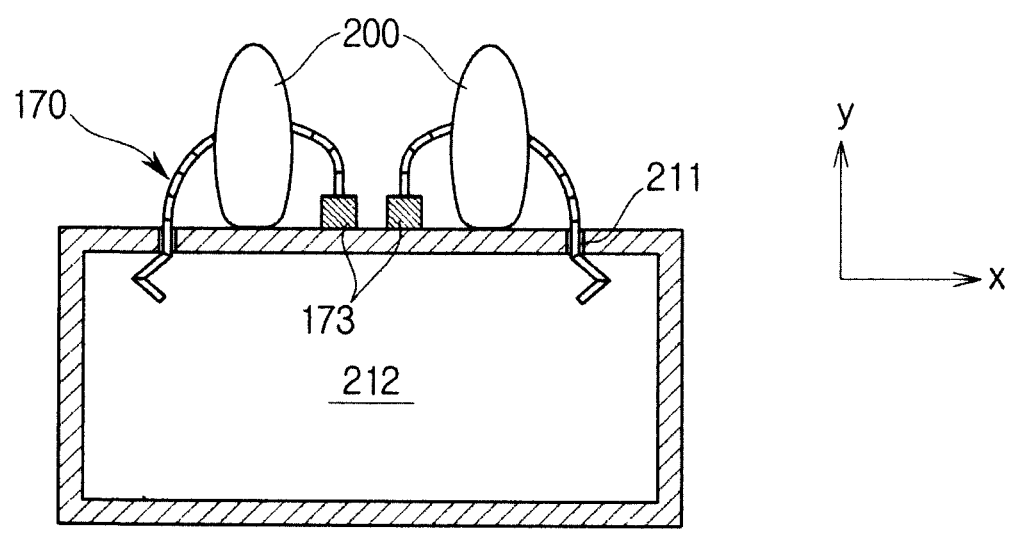

FIGS. 8A and 8B are cross-sectional views of the patient table 210 in the region at which the RF coils are retained. These views illustrate one embodiment with regard to the retention of the RF receiving coil, integrated with the patient table, in the interior receiving space 212 of the patient table 210.

As exemplarily shown in FIG. 8A, the RF receiving coils 170 may be folded and retained in the interior receiving space 212 of the patient table 210. The coils 170 may be extracted from the interior space 212 via pulling on the holders 173 at the top ends of coils 170. The folded RF receiving coils 170 may have a shorter effective length in the folded state, and thus may be stored and retained even within a small interior receiving space 212 of the patient table 210.

To this end, each RF receiving coil 170 may include a plurality of coil panels 171 including coils to receive magnetic resonance signals, and connectors 172 connecting the coil panels in a foldable manner.

Each coil panel 171 may include one or more coils. As a result of providing the plural coil panels 171 to increase a surface area, magnetic resonance signals may be received from a wide region of the object 200.

The connectors 172 may connect the respective coil panels 171 to one another. In particular, the connectors 172 may connect the respective coil panels 171 such that the coil panels 171 are arranged in a given direction. In this case, the coil panels 171 connected by the connectors 172 may be foldable.

Through the above described configuration, the RF receiving coil 170 may be folded and received in the interior receiving space 212 of the patient table 210, forming a zig-zag pattern in cross section in a non-use state. The folded RF receiving coil 170 may be thin, and thus may be easily received even in the narrow receiving space 212. As exemplarily shown in FIGS. 8A and 8B, except for the portion of the RF receiving coil 170 exposed outward of the patient table 210, the remaining portion of the RF receiving coil 170 may be folded and received in the interior receiving space 212 of the patient table 210.

The holder 173 is provided at the end of the RF receiving coil 170 exposed outward of the patient table 210, as described above. Provision of the holder 173 does not affect retraction of the RF receiving coil 170 into the interior receiving space 212 of the patient table 210, and may be applied even if the RF receiving coil 170 is received in a different manner.

The RF receiving coil 170 may be normally received as exemplarily shown in FIG. 8A, and may be extracted outward of the patient table 210 during magnetic resonance imaging. Referring to FIG. 8B, the folded RF receiving coil 170 may be unfolded when extracted. Thereby, since the RF receiving coil 170 may have an increased surface area, magnetic resonance signals may be received from a wide region of the object.

The patient table 210 may have the plural openings 211, e.g., in the top face 214 of the table upon which the object 200 is placed during the MRI procedure. The respective RF receiving coils 170 may be extracted from or otherwise moved outward of the patient table 210 through the openings 211. Movement of the RF receiving coils 170 does not affect a reception manner of the RF receiving coil 170 in the interior receiving space 212 of the patient table 210, and may be applied even if the RF receiving coils 170 are received in a different manner.

If the RF receiving coils 170 are embodied as PV coils, as exemplarily shown in FIG. 8B, the RF receiving coils 170 may come into close contact with the respective legs of the patient 200 to receive magnetic resonance signals from the legs. As the respective RF receiving coils 170 receive MR signals from the respective legs, MR images of the respective legs may be separately produced.

Figure 9A:
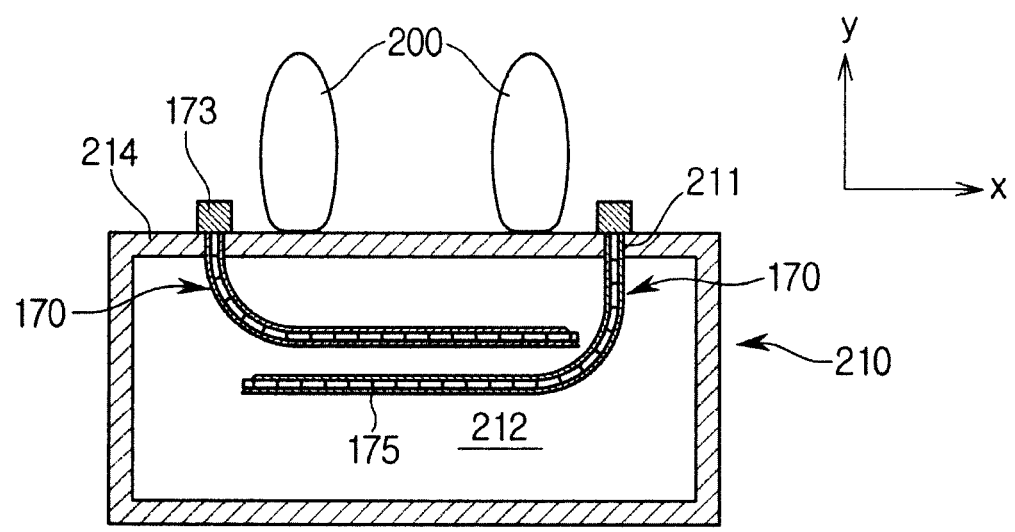
FIG. 9A and FIG. 9B are views illustrating another embodiment of a patient table integrated with at least one RF coil disposed in an interior receiving space of the patient table.
Figure 9B:
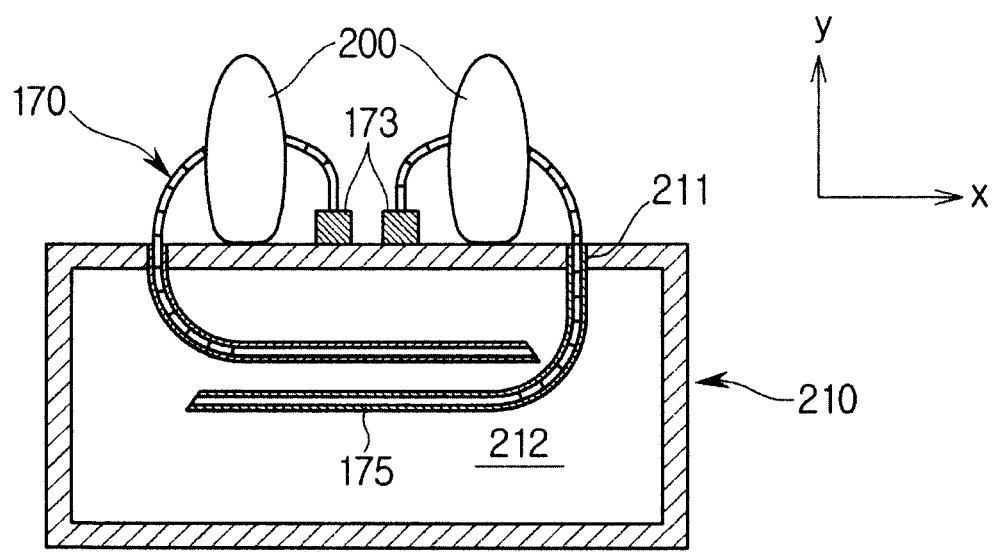

FIGS. 9A and 9B are views illustrating another embodiment of a patient table integrated with at least one RF coil disposed in an interior receiving space of the patient table.

As exemplarily shown in FIG. 9A, a guide 175 may be installed in the interior receiving space 212 of the patient table 210 to guide movement of the RF receiving coil 170. The RF receiving coil 170 may be coupled to the guide 175 and may be received in the interior receiving space 212 of the patient table 210 under guidance of the guide 175. As illustrated, RF receiving coil 170 is retained within the guide 175.

When two RF receiving coils 170 are disposed in the interior receiving space 212 of the patient table 210 as exemplarily shown in FIG. 9A, two guides 175 may be installed at different heights from the bottom surface of the top face 214 of the table. This enables reception and storage of the RF receiving coils 170 in a narrow space.

The guide 175 may include a rail in one embodiment. One side of the RF receiving coil 170 may have a shape suitable for coupling with the rail, and thus may be coupled to the rail. The RF receiving coil 170 coupled to the rail may move along the guide.

The RF receiving coil 170 may be normally retained during non-use as exemplarily shown in FIG. 9A, and may be extracted from the guide 175 and moved outward of the patient table 210 during magnetic resonance imaging. Referring to FIG. 9B, the RF receiving coil 170, received in the receiving space 212 while being coupled to the guide 175, may be moved outward of the patient table 210 while partially retained by the guide 175.

When the patient table 210 has the opening 211 in one face thereof, the guide 175 may extend from the opening 211 to the interior receiving space 212 of the patient table 210. Thereby, the guide 175 assists the RF receiving coil 170 in moving outward of the patient table 210 through the opening 211. That is, the RF receiving coil 170, coupled to the guide 175, may be moved along the guide 175 in the interior receiving space 212. The RF coil may be pulled through the opening 211, and may be moved outward of the patient table 210 through the opening 211.

The respective RF receiving coils 170, moved outward of the patient table 210 on one side while partially retained on the other side by the guides 175, may come into close contact with different regions of the object 200 to receive magnetic resonance signals from the corresponding regions.

Figure 10A:
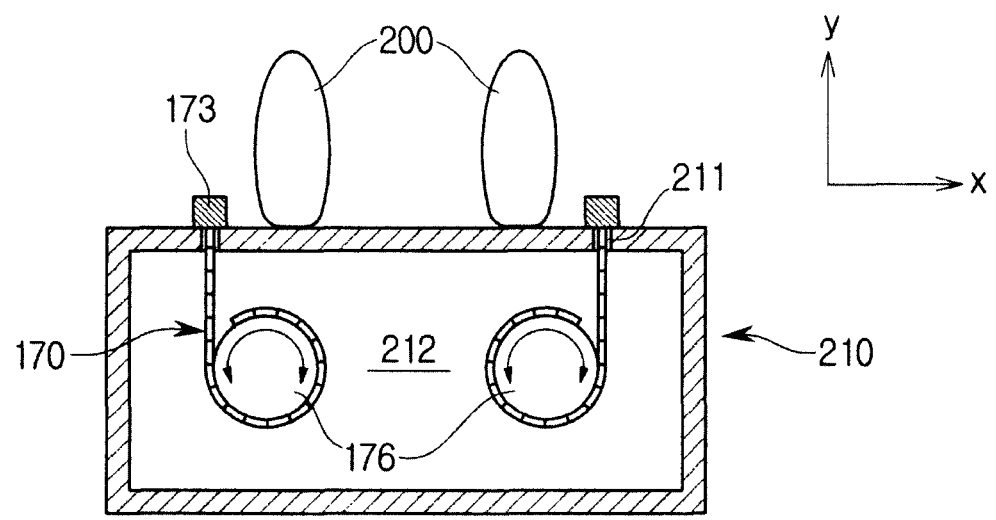
FIG. 10A and FIG. 10B are views illustrating a further embodiment of a patient table integrated with at least one RF receiving coil.
Figure 10B:
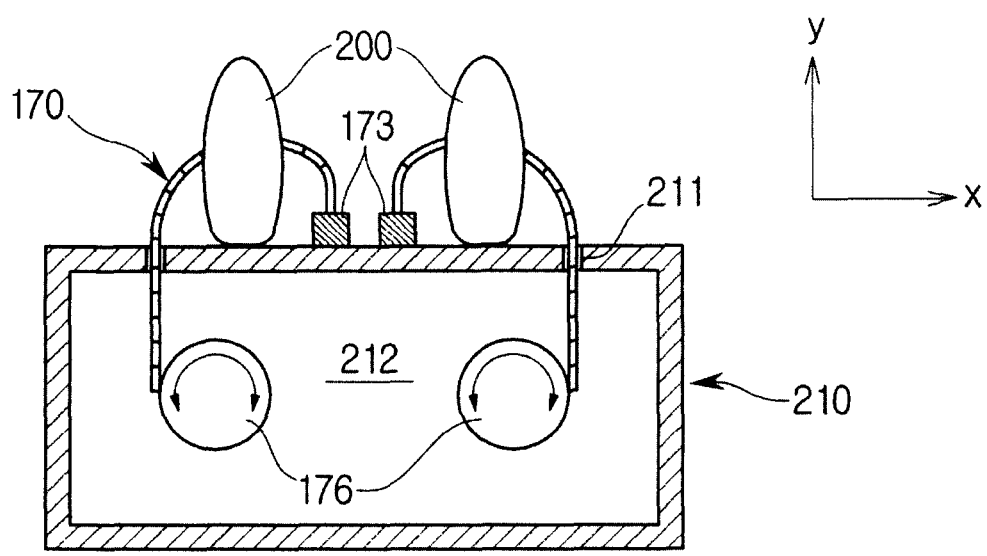

FIGS. 10A and 10B are views illustrating a further embodiment of a patient table integrated with at least one RF receiving coil As exemplarily shown in FIG. 10A, a rotating shaft 176 may be installed in the interior receiving space 212 of the patient table 210. One end of the RF receiving coil 170 may be coupled to the rotating shaft 176 such that the RF receiving coil 170 is fixed in the receiving space 212 during non-use, and retained with one end in a curved state. The RF receiving coil 170 may be received in the receiving space 212 while surrounding a curved surface of the rotating shaft 176. As the rotating shaft 176 is rotated in a direction designated by the curved arrows as exemplarily shown in FIG. 10A, the RF receiving coil 170 may come into contact with the rotating shaft 176, or may be separated from the rotating shaft 176.

When the RF receiving coil 170 is received in the patient table 210 while surrounding the rotating shaft 176, the space occupied by RF receiving coil 170 may be shorter in length, which ensures reception of the RF receiving coil 170 in a narrow space.

FIG. 10A illustrates reception of the two RF receiving coils 170, and thus two rotating shafts 176 may be provided. The number of the rotating shafts 176 may vary based on the number of the RF receiving coils 170.

The RF receiving coil 170 may be normally received as exemplarily shown in FIG. 10A, and may be moved outward of the patient table 210 during magnetic resonance imaging. Referring to FIG. 10B, the RF receiving coil 170, received in the receiving space 212 while surrounding the rotating shaft 176, may be separated from the rotating shaft 176 via rotation of the rotating shaft 176, thereby being moved outward of the patient table 210.

As the RF receiving coil 170, which is arranged in a space of short length while surrounding the rotating shaft 176, is separated from the rotating shaft 176, the exposed surface area of the RF receiving coil 170 may increase, which allows the RF receiving coil 170 to receive magnetic resonance signals from a wide region of the object 200.

The RF receiving coil 170 may better receive MR signals as the RF receiving coil 170 comes into closer contact with the object 200. The RF receiving coil 170, separate from the patient table 200, may come into close contact with the object 200 using a Velcro tape, a strap, or the like. As shown in FIG. 10B, the holders 173 may be affixed to respective points at a central region of the table 210 in the width direction to retain the RF coil 170 in place surrounding the patient.

Figure 11A:
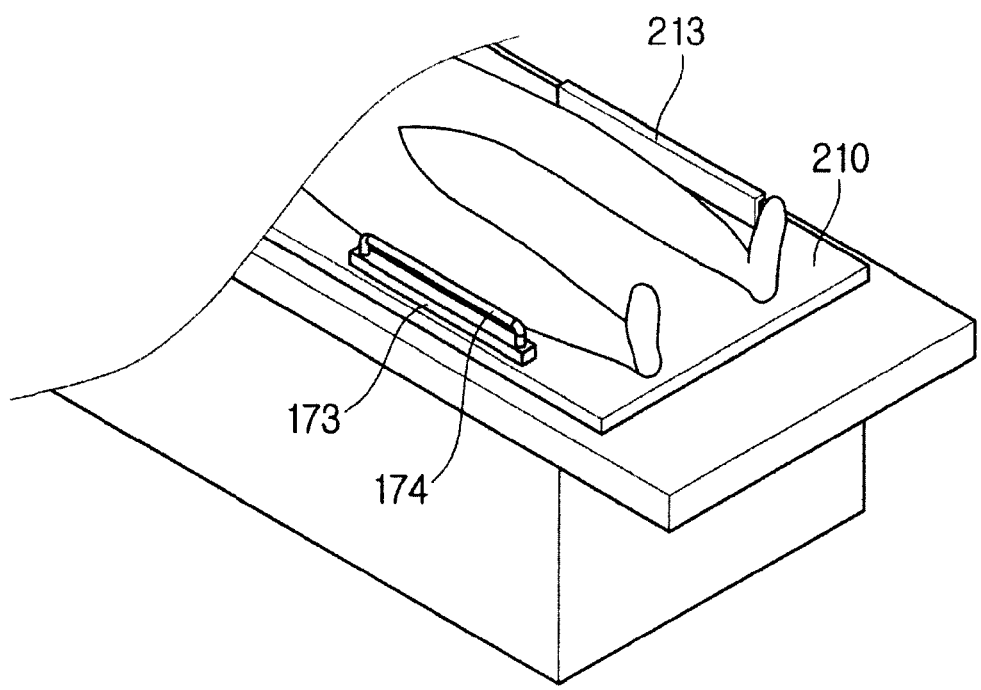
FIG. 11A and FIG. 11B are views illustrating one embodiment of a patient table integrated with at least one RF receiving coil, which includes a fixing piece.
Figure 11B:
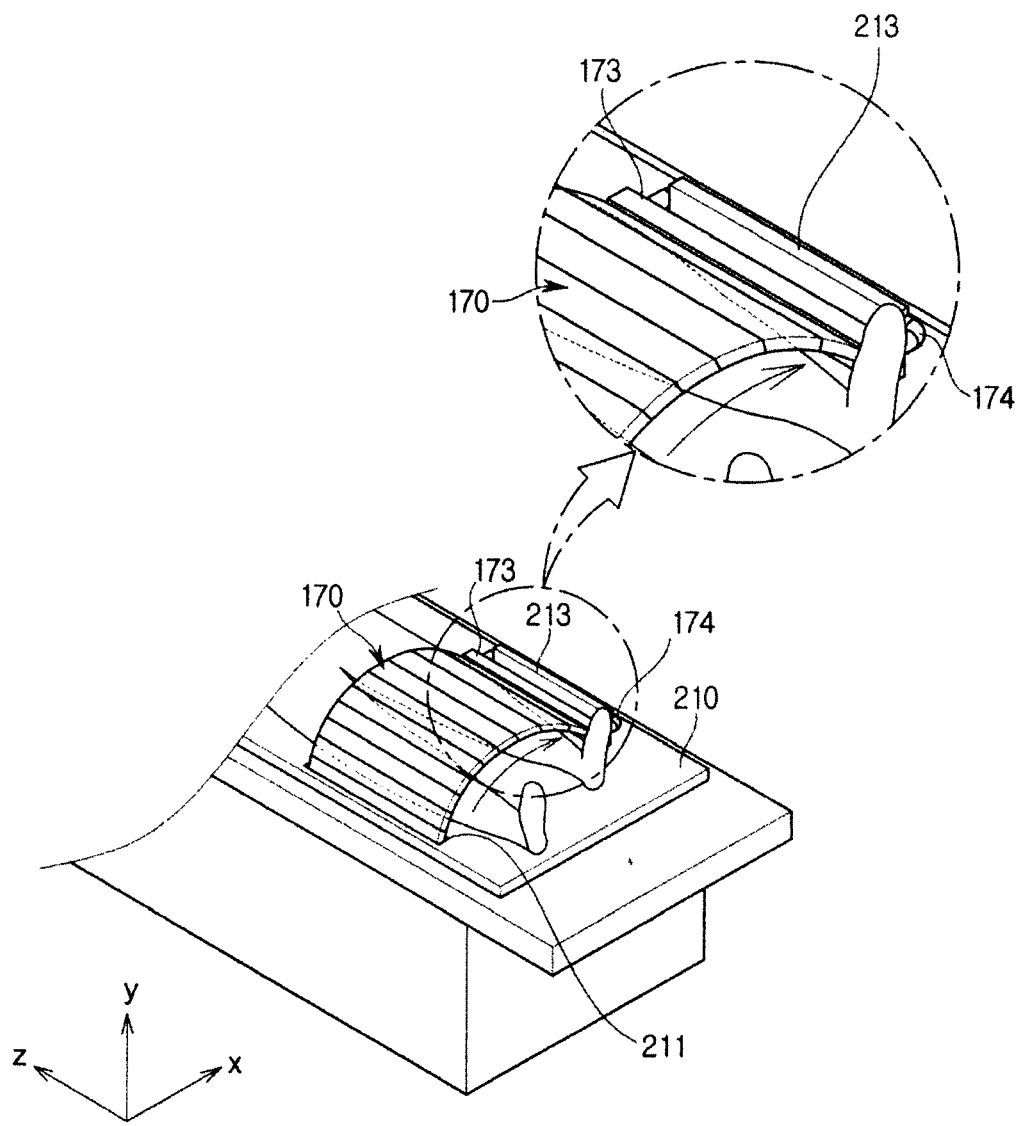

The RF receiving coil 170, integrated with the patient table 210, may include a fixing piece 174 (as shown in FIGS. 11A, 11B) to assist the RF receiving coil 170 in coming into close contact with the object 200. The fixing piece 174 may be installed to one end of the RF receiving coil 170 to fix the end of the RF receiving coil 170.

More specifically, first, the RF receiving coil 170, received in the interior receiving space 212 of the patient table 210, may be moved outward of the patient table 210. Next, to improve the receiving sensitivity of magnetic resonance signals, the RF receiving coil 170 may be brought into close contact with the object 200 to the maximum extent. Finally, in a state in which the RF receiving coil 170 is brought into close contact with the object 200, a position of the RF receiving coil 170 may be fixed using the fixing piece 174.

FIGS. 11A and 11B are views illustrating one embodiment of a patient table integrated with at least one RF receiving coil, which includes a fixing piece.

The patient table 210 may be provided at one face thereof with a first coupling piece 213 for coupling with the fixing piece 174. As the fixing piece 174 is coupled to the first coupling piece 213, a position of the RF receiving coil 170 may be fixed.

As shown in FIG. 11A, the fixing piece 174 may be installed to one face of the holder 173 of the RF receiving coil 170. The first coupling piece 213 may be located on an opposing side of the table 210 as the aperture 211 through which the RF coil 170 is extracted (and is thus opposite to the fixing piece 174 prior to the coil's extraction). A desired region of the object 200 may be located between the fixing piece 174 and the first coupling piece 213 prior to the coil 170 extraction.

It is noted here that the holder 173 may be alternatively omitted, and in this case the fixing piece 174 may be directly installed to one end of the RF receiving coil 170 exposed outward of the patient table 200.

To implement magnetic resonance imaging, after the RF receiving coil 170 retained in the receiving space 212 is moved outward of the patient table 210, the RF receiving coil 170 is brought into close contact with a desired region of the object 200. Then, to fix a position of the RF receiving coil 170 brought into close contact with the corresponding region, the fixing piece 174 may be coupled to the first coupling piece 213 formed at one face of the patient table 210 as exemplarily shown in FIG. 11B. The RF receiving coil 170 coupled to the first coupling piece 213 is fixed while coming into close contact with the corresponding region of the object 200, so that MR signals can be stably received from the corresponding region.

Instead of the RF receiving coil 170 being directly coupled to the patient table 210, it may be fixed via coupling to an auxiliary fixing member of the patient table 210.

Figure 12A:
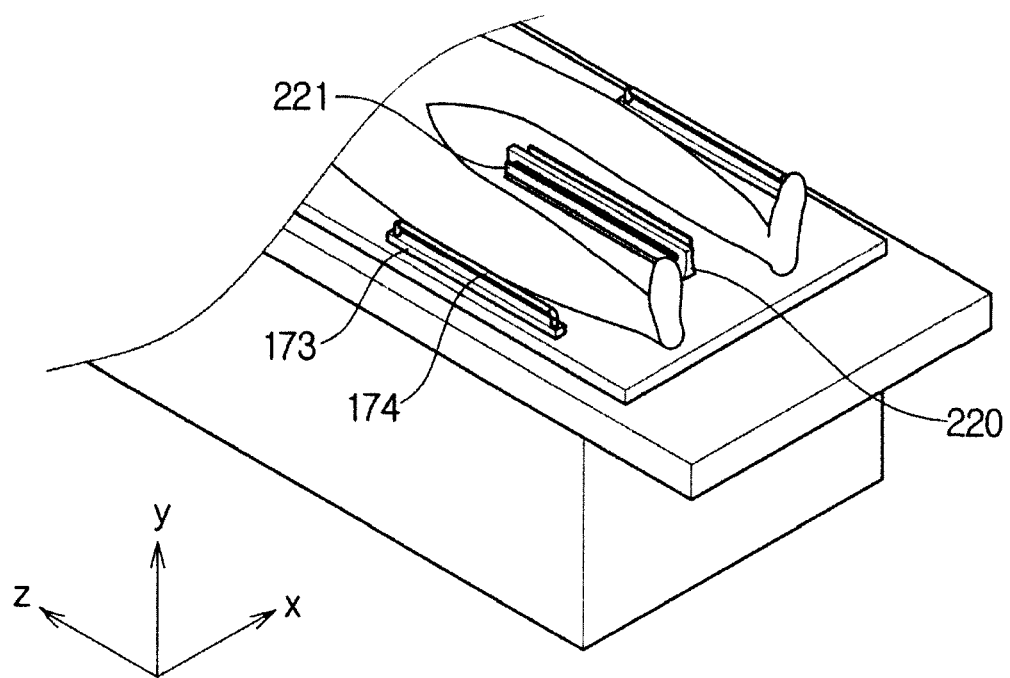
FIG. 12A and FIG. 12B are views illustrating another embodiment of a patient table integrated with at least one RF receiving coil, which employs a fixing piece.
Figure 12B:
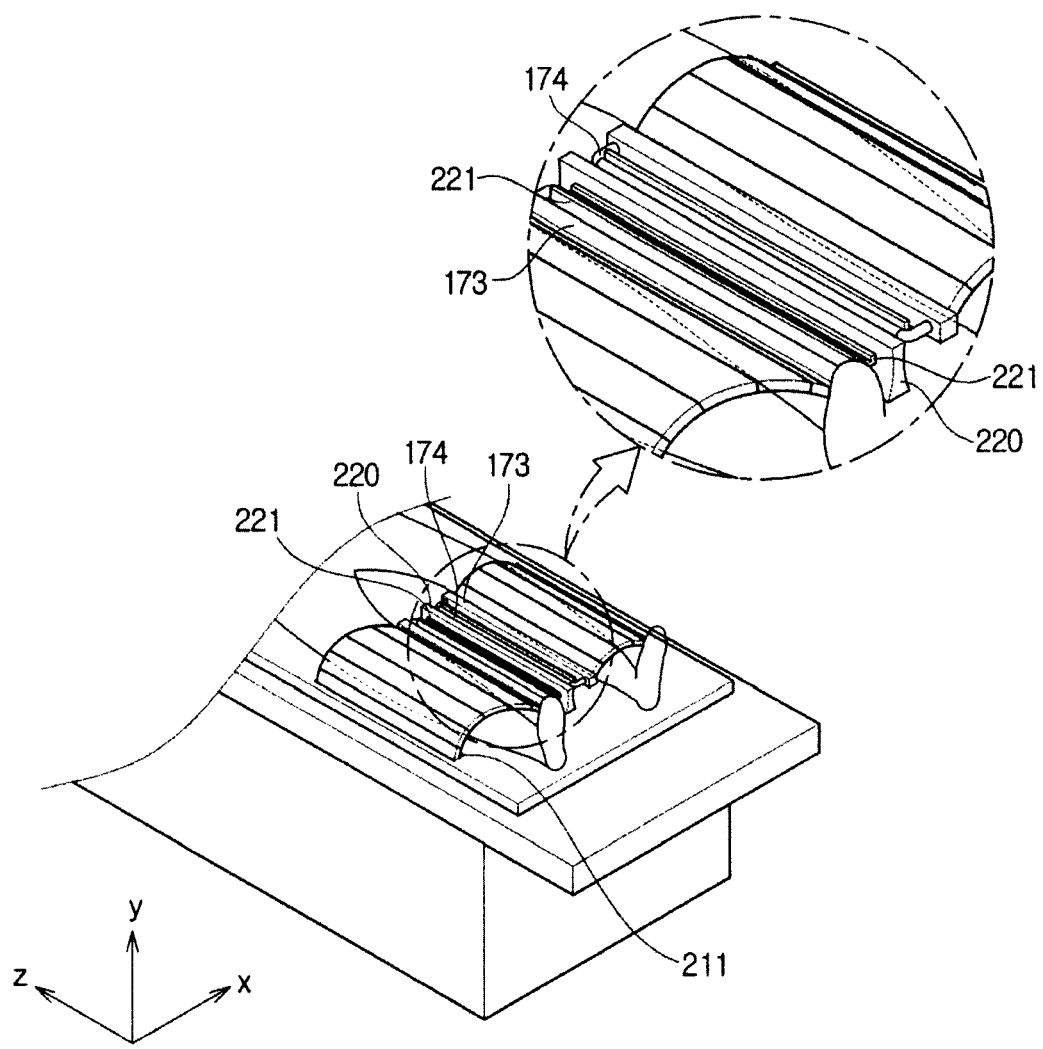

FIGS. 12A and 12B are views illustrating another embodiment of a patient table integrated with at least one RF receiving coil, which employs a fixing piece. Here, an auxiliary fixing member 220 may be separably coupled (i.e., attachable but easily removable) to one face of the patient table 210. The separation/coupling mechanism of the auxiliary fixing member 220 may be any suitable mechanism, preferably to enable an operator to easily perform the coupling and separation as needed.

The auxiliary fixing member 220 may include a second coupling piece 221 for coupling with the fixing piece 174 of the RF receiving coil 170. Thus, after the RF receiving coil 170 is moved to a selected position, the fixing piece 174 of the RF receiving coil 170 may be coupled to the second coupling piece 212 of the auxiliary fixing member 220 to fix a position of the RF receiving coil 170.

As exemplarily shown in FIG. 12A, the auxiliary fixing member 220 may be located between two RF receiving coils 170. In one embodiment of the auxiliary fixing member 220, the auxiliary fixing member 220 may be located between the legs of a patient 200 lying on the patient table 210. The auxiliary fixing member 220 may be coupled to the patient table 210 at a selected position.

As the auxiliary fixing member 220 is coupled to the fixing piece 174, a position of the RF receiving coil 170 may be fixed as exemplarily shown in FIG. 12B. More specifically, the RF receiving coil 170 may be moved outward of the patient table 210 and thereafter brought into close contact with a corresponding region of the object 200. Thereafter, as the second coupling piece 221 of the auxiliary fixing member 220 is coupled to the fixing piece 174 of the RF receiving coil 170, a position of the RF receiving coil 170 may be fixed.

Fixing the RF receiving coil 170 brought into close contact with the corresponding region of the object 200 may improve the receiving sensitivity of magnetic resonance signals, resulting in production of a high-resolution magnetic resonance image.

As noted earlier, conventionally, an RF receiving coil stored separately from the patient table, and is connected to the patient table via a cable during magnetic resonance imaging. Magnetic resonance signals, received by the RF receiving coil, are transmitted to the image processor connected to the patient table via the cable, and the image processor produces a magnetic resonance image based on the magnetic resonance signals. The conventional cable connecting the RF receiving coil and the patient table is exposed to the exterior of the patient table, thus having a high risk of damage.

In the present embodiments, the above-noted hazard may be avoided as the RF receiving coil 170, integrated with the patient table 210, may be electrically connected to the image processor 160 through a cable provided within the patient table 210.

Figure 13:
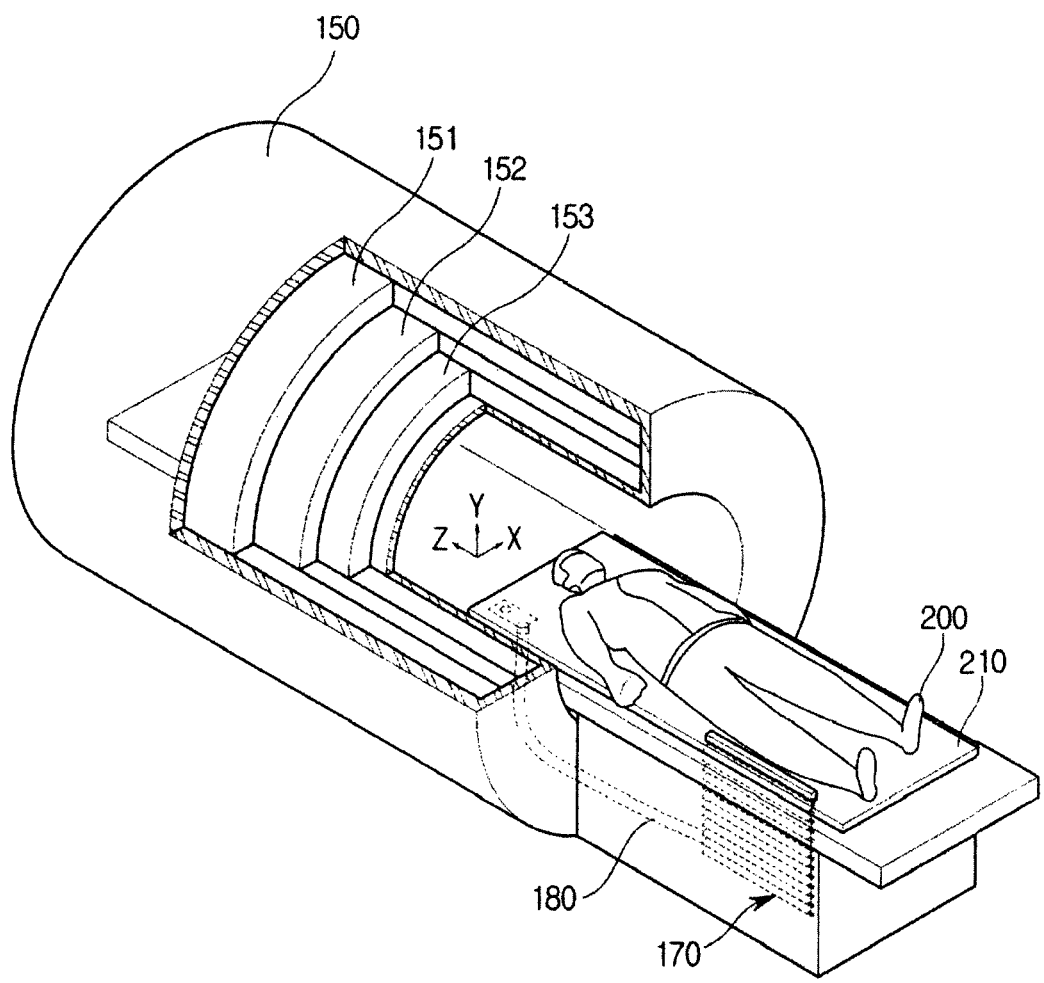
FIG. 13 is a view showing one embodiment with regard to connection between the RF receiving coil, integrated with the patient table, and the patient table.

FIG. 13 is a view showing one embodiment of an MRI apparatus including a patient table with at least one integrated RF receiving coil and a connection cable within the table. As in the embodiments described above, the RF receiving coil 170 may be received in the interior receiving space 212 of the patient table 210. In addition, the RF receiving coil 170, received in the patient table 210, may be connected to the image processor 160 through a cable 180 within the patient table 210.

As shown in FIG. 13, the RF receiving coil 170, received in the patient table 210, may be connected to a connector mounted on the patient table 210 via the cable 180. To this end, the cable 180 may be received in the patient table 210.

The cable 180 may be a separate internal component of the patient table 210, or may be integrated with the RF receiving coil 170. In the illustrated example, the cable 180 connects the RF receiving coil 170 and the patient table 210 connector to each other.

As exemplarily shown in FIG. 13, when the cable 180 is provided in the patient table 210, the cable 180 is not exposed outward of the patient table 210 and thus has less risk of damage. As a result, the cable 180 may stably transmit magnetic resonance signals received by the RF receiving coil 170 to the image processor 160, enabling production of a more vivid magnetic resonance image based on the magnetic resonance signals.

As is apparent from the above description, according to one aspect of an RF receiving coil and a MRI apparatus including the same, the RF receiving coil may be integrated with a patient table to receive magnetic resonance signals. This may eliminate an additional laborious task to move the RF receiving coil to the patient table and to connect the RF receiving coil and a patient table connector to each other.

According to another aspect of the RF receiving coil and the MRI apparatus including the same, the RF receiving coil may be fixed to a surface of the patient table (for example, via a fixing member attached to a face of the patient table), to facilitate production of a high-resolution magnetic resonance image.

According to a further aspect of the RF receiving coil and the MRI apparatus including the same, a cable, connecting the RF receiving coil and a patient table connector, may be provided in the patient table, which may minimize damage to the cable.

Although the embodiments of the present invention have been shown and described, it would be appreciated by those skilled in the art that changes may be made in these embodiments without departing from the principles and spirit of the invention, the scope of which is defined in the claims and their equivalents.

What is claimed is:
1. A magnetic resonance imaging apparatus comprising:
a patient table having an interior space; and
at least one Radio Frequency (RF) receiving coil integrated with the patient table and retained in the space, the RF receiving coil being movable outward of the patient table,
wherein the RF receiving coil comprises a plurality of coil panels including coils to receive magnetic resonance signals, and connectors connecting the plurality of coil panels to one another in a foldable manner.

2. The apparatus according to claim 1, wherein the patient table has at least one aperture formed in a face thereof, and wherein one end of the RF receiving coil is exposed through the aperture, and the RF coil being extractable and retractable through the aperture.

3. The apparatus according to claim 2, wherein the RF receiving coil includes a holder affixed to the exposed end thereof to prevent the exposed end from being introduced into the receiving space through the aperture.

4. The apparatus according to claim 1, wherein the RF receiving coil is folded when retained in the space.

5. The apparatus according to claim 1, wherein the patient table includes a guide disposed in the space to guide movement of the RF receiving coil.

6. The apparatus according to claim 1, wherein the RF receiving coil includes a fixing piece installed to one end thereof, exposed at an exterior of the patient table, to fix the exposed end to a surface of the patient table.

7. The apparatus according to claim 6, wherein the patient table includes a first coupling piece provided at the surface thereof, the first coupling piece being coupled to the fixing piece to fix the RF receiving coil.

8. The apparatus according to claim 6, further comprising an auxiliary fixing member to fix the RF receiving coil, wherein the auxiliary fixing member is removably attached to the surface of the patient table.

9. The apparatus according to claim 8, wherein the auxiliary fixing member includes a second coupling piece coupled to the fixing piece to fix the RF receiving coil.

10. The apparatus according to claim 1, further comprising a cable provided in the patient table to transmit a magnetic resonance signal, received from an object by the RF receiving coil, to an image processor.

11. The apparatus according to claim 1, wherein the RF receiving coil includes a peripheral vascular (PV) coil.

12. An RF receiving coil comprising:
a plurality of coil panels including coils to receive magnetic resonance signals; and
connectors to connect the coil panels to one another in a foldable manner,
wherein the RF receiving coil is integrated with a patient table so as to be folded when retained in the patient table, and
wherein the coil panels are extractable from an interior of the patient table to an outside of the patient table through an aperture in the patient table.

13. The RF receiving coil according to claim 12, further comprising a holder installed to one end of the RF receiving coil exposed outward of the patient table to prevent the exposed end of the RF receiving coil from being introduced into a space of the patient table through the aperture.

14. The RF receiving coil according to claim 12, further comprising a fixing piece installed to one end of the RF receiving coil to fix the coil panels to a surface of the patient table.

15. A patient table for a magnetic resonance imaging apparatus comprising:
a base portion;
an upper face atop the base portion, the upper face having at least one aperture; and
at least one Radio Frequency (RF) receiving coil integrated with the patient table and retained in a region of the base portion, the RF receiving coil being extractable and retractable through the at least one aperture,
wherein the RF receiving coil comprises a plurality of coil panels including coils to receive magnetic resonance signals, and connectors connecting the plurality of coil panels to one another in a foldable manner.

* * * * *